(12) United States Patent
Ekman et al.

(10) Patent No.: US 9,227,016 B2
(45) Date of Patent: Jan. 5, 2016

(54) AUTO-INJECTOR WITH A TORSION SPRING

(75) Inventors: Matthew Ekman, Macclesfield (GB); Thomas Mark Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 177 days.

(21) Appl. No.: 13/877,497

(22) PCT Filed: Oct. 6, 2011

(86) PCT No.: PCT/EP2011/067489
§ 371 (c)(1),
(2), (4) Date: Jun. 24, 2013

(87) PCT Pub. No.: WO2012/045828
PCT Pub. Date: Apr. 12, 2012

(65) Prior Publication Data
US 2013/0274676 A1 Oct. 17, 2013

(30) Foreign Application Priority Data
Oct. 8, 2010 (EP) .................................. 10186982

(51) Int. Cl.
*A61M 5/20* (2006.01)
*A61M 5/315* (2006.01)
*A61M 5/32* (2006.01)

(52) U.S. Cl.
CPC ......... *A61M 5/2033* (2013.01); *A61M 5/31513* (2013.01); *A61M 5/3202* (2013.01);
(Continued)

(58) Field of Classification Search
CPC ............ A61M 5/2033; A61M 5/3202; A61M 5/3243; A61M 5/46; A61M 5/326; A61M 2005/202; A61M 2005/208; A61M 2005/2086; A61M 2005/3261; A61M 2005/3263; A61M 5/3271; A61M 5/3272; A61M 5/31528; A61M 2005/3152; A61M 2005/2013
USPC .......... 604/110, 130, 135, 187, 192, 197, 198
See application file for complete search history.

(56) References Cited

U.S. PATENT DOCUMENTS

| | | | |
|---|---|---|---|
| 7,112,187 B2 * | 9/2006 | Karlsson ........................ | 604/187 |
| 7,740,618 B2 * | 6/2010 | Markussen .................... | 604/208 |

(Continued)

FOREIGN PATENT DOCUMENTS

| | | | | |
|---|---|---|---|---|
| WO | 02/17996 | | 3/2002 | |
| WO | WO 2004078239 A1 * | | 9/2004 | ............ A61M 5/315 |

(Continued)

OTHER PUBLICATIONS

International Search Report for Int. App. No. PCT/EP2011/067489, completed Jan. 23, 2012.

*Primary Examiner* — Nicholas Lucchesi
*Assistant Examiner* — Justin L Zamory
(74) *Attorney, Agent, or Firm* — Fish & Richardson P.C.

(57) ABSTRACT

The invention relates to an auto-injector for administering a dose of a liquid medicament (M), comprising of an elongate housing arranged to contain a syringe with a hollow needle and a bung for sealing the syringe and displacing the medicament (M), the elongate housing having a distal end (D) and a proximal end (P) with an orifice intended to be applied against an injection site, wherein the syringe is slidably arranged with respect to the housing; spring means capable of, upon activation, pushing the needle from a covered position inside the housing into an advanced position through the orifice and past the proximal end (P) as well as operating the syringe to supply the dose of medicament (M); and activating means arranged to lock the spring means in a pressurized state prior to manual operation and capable of, upon manual operation, releasing the spring means for injection. The spring means is a torsion spring grounded at one end in the housing and at the other end in a first gear member rotatable about a longitudinal axis but axially fixed wherein the first gear member, upon rotation, is arranged for translatively moving a second gear member, the second gear member prevented from rotating and coupled to the bung in order to push it towards the proximal end (P), wherein the first gear member is engaged with the activating means prior to manual operation in a manner to prevent rotation and disengaged from the activating means upon manual operation. The activating means is a trigger button, arranged at a distal end (D) of the housing and operable by being pressed in proximal direction (P).

14 Claims, 5 Drawing Sheets

(52) U.S. Cl.
CPC ............ *A61M 5/326* (2013.01); *A61M 5/3271* (2013.01); *A61M 2005/206* (2013.01); *A61M 2005/208* (2013.01); *A61M 2005/3247* (2013.01)

(56) References Cited

U.S. PATENT DOCUMENTS

2002/0095120 A1* 7/2002 Larsen et al. ................ 604/187
2006/0287630 A1 12/2006 Hommann
2010/0114025 A1* 5/2010 Moller ........................ 604/135
2010/0234811 A1* 9/2010 Schubert et al. ............. 604/198

FOREIGN PATENT DOCUMENTS

| WO | 2009/007305 | 1/2009 |
| WO | 2009/037141 | 3/2009 |
| WO | 2009/098502 | 8/2009 |

* cited by examiner

AUTO-INJECTOR WITH A TORSION SPRING

CROSS REFERENCE TO RELATED APPLICATIONS

The present application is a U.S. National Phase Application pursuant to 35 U.S.C. §371 of International Application No. PCT/EP2011/067489 filed Oct. 6, 2011, which claims priority to European Patent Application No. 10186982.4 filed Oct. 8, 2010. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The European Patent Application EP 10153985.6 discloses an auto-injector for administering a dose of a liquid medicament, comprising:

an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing, spring means capable of, upon activation, pushing the needle from a covered position inside the housing into an advanced position through the orifice and past the proximal end as well as operating the syringe to supply the dose of medicament, activating means arranged to lock the spring means in a pressurized state prior to manual operation and capable of, upon manual operation, releasing the spring means for injection.

The spring means is a torsion spring grounded at one end in the housing and at the other end in a first gear member rotatable about a longitudinal axis but axially fixed. The first gear member, upon rotation, is arranged for translatively moving a second gear member. The second gear member is prevented from rotating and coupled to the bung in order to push it towards the proximal end. The first gear member is engaged with the activating means prior to manual operation in a manner to prevent rotation and disengaged from the activating means upon manual operation. When the torsion spring is released by operating the activating means the first gear member starts rotating.

SUMMARY

It is an object of the present invention to provide an improved auto-injector.

The object is achieved by an auto-injector according to claim 1.

Preferred embodiments of the invention are given in the dependent claims.

An auto-injector for administering a dose of a liquid medicament according to the invention comprises:

an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing, spring means capable of, upon activation, pushing the needle from a covered position inside the housing into an advanced position through the orifice and past the proximal end as well as operating the syringe to supply the dose of medicament, activating means arranged to lock the spring means in a pressurized state prior to manual operation and capable of, upon manual operation, releasing the spring means for injection.

In the context of this patent application the term proximal refers to the direction pointing towards the patient during an injection while the term distal refers to the opposite direction pointing away from the patient.

According to the invention the spring means is a torsion spring grounded at one end in the housing and at the other end in a first gear member rotatable about a longitudinal axis but axially fixed. The first gear member, upon rotation, is arranged for translatively moving a second gear member. The second gear member is prevented from rotating and coupled to the bung in order to push it towards the proximal end. The first gear member is engaged with the activating means prior to manual operation in a manner to prevent rotation and disengaged from the activating means upon manual operation. The torsion spring is preferably loaded or wound during manufacturing of the auto-injector. When the torsion spring is released by operating the activating means the first gear member starts rotating.

The single torsion spring is used for both inserting the needle and fully emptying the syringe. A major advantage of the torsion spring and the gear is that force is exerted on the bung and syringe in a smooth manner, whereas a conventional compression spring exhibits a rather abrupt force deployment which may spoil a glass syringe or other parts of the auto-injector.

According to the invention the activating means is a trigger button arranged at a distal end of the housing and operable by being pressed in proximal direction. This allows actuation of the auto-injector by a user grabbing it and pushing the trigger button with their thumb or other means.

In one embodiment an essentially tube-shaped needle shroud is arranged around the syringe in the housing. The needle shroud is slidable between at least a retracted position with the needle shroud almost hidden inside the housing and an advanced position with the needle shroud protruding from the proximal end and covering the hollow needle in its advanced position. The needle shroud is biased by a second spring means towards the advanced position and locked in the retracted position by a locking means which is releasable by rotary movement transmitted from the first gear member through a clutch mechanism which is engaged by the second gear member shortly before the second gear member is fully advanced during an injection stroke. Hence, once the dose is complete, the second spring means returns the needle shroud over the needle. This makes the device safer than an equivalent manual injection with respect to needlestick injuries.

An interlock mechanism may be arranged for locking the activating means and preventing it from accidental operation. The interlock mechanism may be coupled to the needle shroud. The interlock mechanism may be releasable by pushing the needle shroud a small distance into the housing from the needle shroud's retracted position. Thus, the device cannot be used until the needle shroud is depressed. In normal use this would occur by pushing the device against an injection site, i.e. a patient's skin.

The trigger button may have a locking pin engageable with at least one dog tooth provided on the first gear member for preventing rotation thereof in order to lock the spring means or keep it locked in a pressurized state. The dog teeth may be circumferentially arranged at the first gear member thus allowing for stopping the rotation and consequently the injection at any point in time by releasing the trigger button. The trigger button may therefore be biased by a return spring.

The shroud locking means may have the shape of a bayonet fit between the needle shroud and an outer rear tube, which is arranged around the torsion spring. The needle shroud is guided in the housing in a manner to prevent relative rotation, e.g. by at least one spline engaging a respective slot in the housing. The outer rear tube is coupled to the clutch mechanism and may therefore be rotated by the torsion spring. The bayonet fit comprises a bayonet pin and a corresponding pin track arranged between the outer rear tube and the needle shroud. The pin may be held behind a track shoulder in order to hold the needle shroud in its retracted position. In order to release the needle shroud the outer rear tube is rotated by a small angle thus turning the bayonet pin away from the track shoulder (or vice versa) and into a straight longitudinal part of the pin track so the compression spring may forward the needle shroud as soon as the auto-injector is removed from the injection site.

The second gear member may be a piston rod having an external lead screw thread. The piston rod may have an axial bore for slidably arranging the piston rod on a shaft attached to the housing. The axial bore and the shaft may have corresponding non-circular profiles in order to prevent relative rotation, e.g. square profiles or profiles with at least one spline or flat. The shaft may be directly or indirectly attached to the housing, e.g. by an end cap. However, the shaft has to be secured against rotation relative to the housing.

The first gear member may be a lead nut engaged with the external lead screw thread of the second gear member. The lead nut may have an internal lead screw thread or a pin guided in the external lead screw thread of the piston rod. Preferably the lead nut is equipped with at least one ball bearing in order to achieve a low friction contact.

In one embodiment the external lead screw thread may have a variable pitch. Thus, speed and force of the needle insertion and injection of the medicament may be adapted to user convenience and to the fact that the torque of the torsion spring is highest when it is fully loaded and lowest near the end of the injection stroke. E.g. the pitch of the thread may be adapted to ensure a quick needle insertion and a relatively slow injection of the medicament in order to cause the least possible pain for the patient.

The interlock mechanism may comprise a flange on the outer rear tube arranged to prevent translation of the trigger button prior to translation of the needle shroud into the housing from the retracted position. The pin track of the bayonet fit may comprise a cam surface arranged to be engaged by the bayonet pin on translation of the needle shroud from the retracted position into the housing in such a manner that the outer rear tube is rotated. This rotation removes the flange so as to allow translation of the trigger button. In order to allow the needle shroud to be pushed back from the retracted position a small clearance may be provided in the pin track behind the track shoulder.

In a preferred embodiment the syringe is arranged in a syringe carrier and supported by the syringe carrier at a proximal end. Supporting the syringe at its proximal end rather than at its flanges avoids damaging the syringe under load since the flanges are more fragile, in particular in a glass syringe. The syringe carrier is slidably arranged in the needle shroud. An abutment is provided in the needle shroud defining a maximum forward position of the syringe carrier. This allows for defining an injection depth, e.g. for a subcutaneous or intramuscular injection.

The clutch mechanism for releasing the needle shroud towards the end of the injection may comprise a circumferential shoulder arranged on the second gear member, e.g. at its distal end, and at least one resilient clutch finger or a number of resilient clutch fingers with respective inclined inner surfaces arranged on a distal end of the first gear member. The shoulder is arranged for increasingly pressing against the inclined surfaces when forwarded thereby flexing the clutch fingers outward near the end of an injection stroke. The clutch mechanism further comprises an inner rear tube arranged around the clutch fingers inside the torsion spring and attached to the outer rear tube at their distal ends. The inner rear tube has a number of internal longitudinal splines for engaging the flexed-out clutch fingers. Prior to being flexed out by the shoulder the first gear member, i.e. the lead nut and its clutch fingers spin without engaging the longitudinal splines of the inner rear tube. When the clutch fingers are flexed out radially they engage with the longitudinal splines in the inner rear tube. Thus the rotation of the first gear member is forwarded to the bayonet fit so the bayonet pin comes clear of the track shoulder and gets into the straight longitudinal part of the pin track thus allowing the needle shroud to slide forward when removed from the injection site. The clutch fingers may have respective external teeth protruding radially outwardly in order to provide a defined engagement with the longitudinal splines.

In a preferred embodiment the internal longitudinal splines are arranged in a manner to form a limited torque drive when engaged with the clutch fingers. This allows for continued rotation of the lead nut even after the outer rear tube has been rotated and consequently the bayonet pin has hit the side of the longitudinal part of the pin track so the bung may be further forwarded until it bottoms out in the syringe so dead volume is avoided. This is particularly advantageous as it ensures improved dose accuracy and no wastage of expensive medicaments as the syringe or cartridge is fully emptied. By contrast a purely positive locking engagement between the clutch fingers and the longitudinal splines would stall the rotary movement as soon as the bayonet pin hits the side of the longitudinal part of the pin track. Furthermore the limited torque engagement can be arranged to provide an acoustic feedback as the clutch fingers 'jump' over the longitudinal splines for the user announcing the upcoming end of the injection. During the injection time, e.g. ten seconds the user is asked to keep pressure on the injection site.

As the user withdraws the auto-injector from the injection site after the end of injection the needle shroud is pushed over the needle by the compression spring into its advanced position. A locking mechanism may be provided for locking the needle shroud in its advanced position so the needle cannot be re-exposed and needle stick injuries with the now contaminated needle are avoided.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
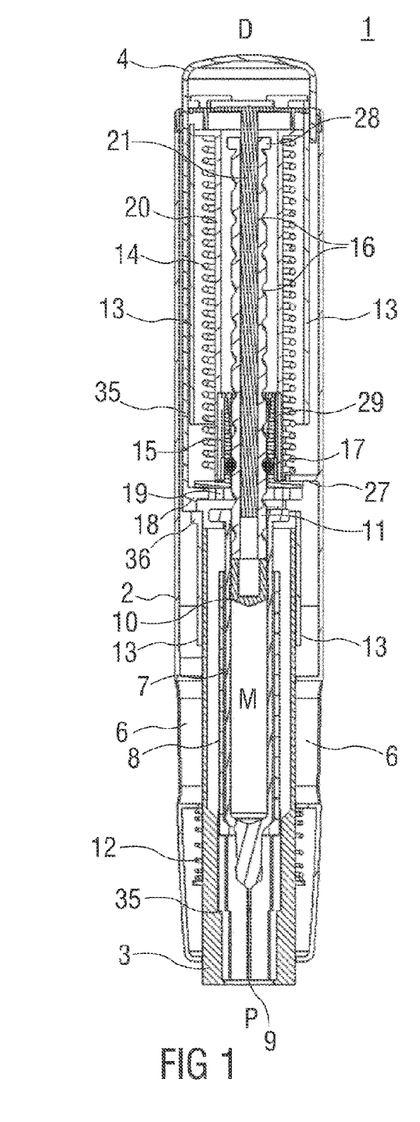
FIG. 1 is a longitudinal section of an auto-injector with a needle shroud and a trigger button arranged at a distal end in a prior to use state.

FIG. 1 shows a longitudinal section of an auto-injector 1 with an elongate housing 2 and a needle shroud 3 for protecting a needle 9. The auto-injector 1 is in a prior to use state. A trigger button 4 for starting an injection is arranged at a distal end D of the auto-injector 1. The trigger button 4 is interlocked with the needle shroud 3 so it cannot be pressed until the needle shroud 3 is pushed into the housing 2 by placing it on an injection site, e.g. a patient's skin and applying pressure. The needle shroud 3 has longitudinal splines (not illustrated) engaged in corresponding grooves in the housing 2 for preventing relative rotation of the needle shroud 3 with respect to the housing 2. A viewing window 6 allows for viewing and inspecting a syringe held in the auto-injector 1.

The syringe 7 is partially surrounded and supported at a front end by a syringe carrier 8. Attached at the front end of the syringe 7 is a hollow needle 9 for piercing a patient's skin and delivering a liquid medicament M stored inside the syringe 7. Near the distal end of the syringe 7 a bung 10 is arranged for sealing and containing the medicament M. The bung 10 may be advanced by a piston rod 11 in order to expel the medicament M from the syringe 7. The syringe carrier 8 is slidably arranged inside the needle shroud 3. The needle shroud 3 is biased by a compression spring 12 towards a proximal end P of the auto-injector 1. A bayonet fit (shown in FIGS. 4, 5, and 6) between the needle shroud 3 and an outer rear tube 13 serves for holding the needle shroud 3 in a retracted position against the bias of the compression spring 12 prior to use, thus enabling the patient to grab and remove a rubber needle shield (not shown) arranged for protecting the needle 9. The bayonet fit comprises a bayonet pin 32 arranged on an outer surface of the needle shroud 3 engaged in a cam track 33 in the outer rear tube 13.

A torsion spring 14 is arranged inside the outer rear tube 13 and with one end attached to a distal end D of the housing 2 so torque from the torsion spring 14 is reacted into the housing 2. The other end of the torsion spring 14 is coupled to a lead nut 15 which is rotatably mounted around the piston rod 11. The piston rod 11 has an external lead screw thread 16 engaged with the lead nut 15. The lead nut 15 is equipped with at least one ball bearing 17 for this engagement. It could alternatively have at least one pin. In the prior to use state shown in FIG. 1 the lead nut 15 is biased by the torsion spring 14 but kept from rotating by a locking pin 18 arranged at a longitudinal bar 35 of the trigger button 4, the locking pin 18 engaged with a dog tooth 19 arranged at the lead nut 15. In the prior to use state the trigger button 4 is interlocked with the needle shroud 3 in a manner to prevent actuation of the trigger button 4 without prior actuation of the needle shroud 3. The longitudinal bar 35 of the trigger button 4 is prevented from translating in proximal direction P by abutting against a stop 36 arranged on the outer rear tube 13 thus also preventing the trigger button 4 from being depressed and the locking pin 18 and the dog tooth 19 from disengaging. The trigger button 4 is splined in the housing 2, resolving the load of the torsion spring 14 statically.

An inner rear tube 20 is arranged inside the torsion spring 14 and around the piston rod 11 and part of the lead nut 15. The piston rod 11 is guided along a shaft 21 arranged in an axial bore of the piston rod 11. The axial bore and the shaft 21 both have a non-circular profile in order to keep the piston rod 11 from rotating, e.g. a square profile or a profile with at least one spline or flat. At its distal end the shaft 21 is attached to the housing 2 in a manner to prevent relative rotation.

A protective needle shield (not shown) may be provided which has to be removed prior to use by a user resulting in the situation of FIG. 1. In this situation the needle 9 is a safe distance back within the needle shroud 3 to protect the user from accidental needlestick injuries.

Figure 2:
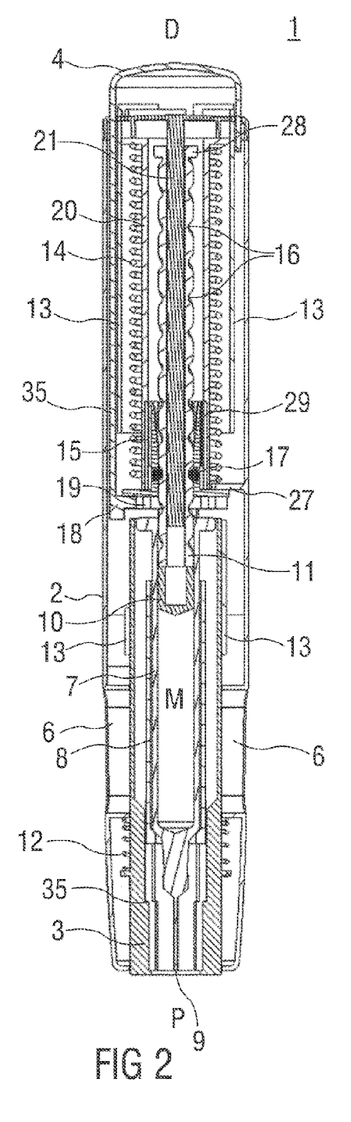
FIG. 2 is a longitudinal section of the auto-injector with the needle shroud translated in distal direction.
Figures 4, 5:
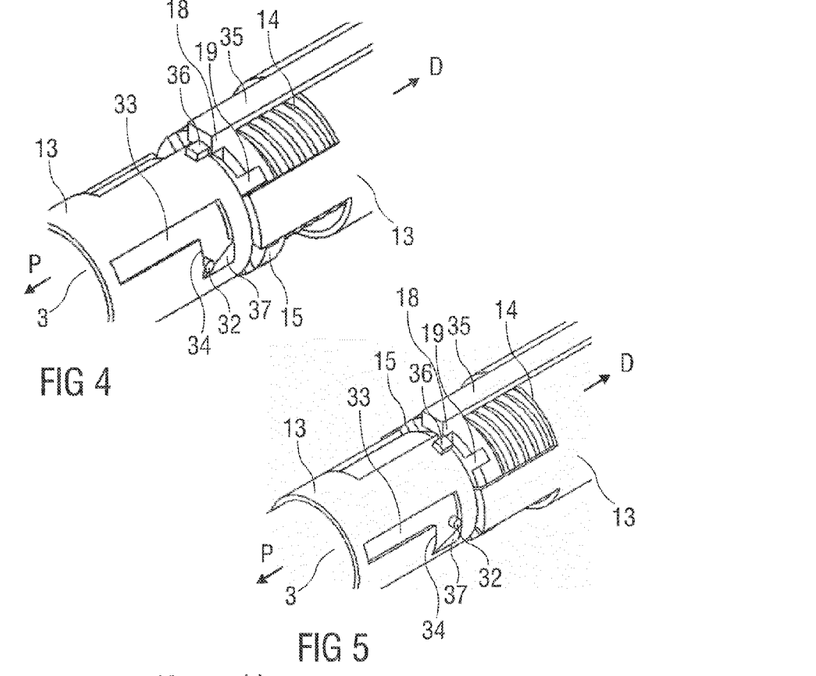
FIG. 4 is a perspective detail view in the prior to use state.
FIG. 5 is a perspective detail view with the needle shroud translated in distal direction and a trigger button interlock released.

In order to prepare for an injection the user pushes the proximal end P of the auto-injector 1 against the injection site. Thus the needle shroud 3 is moved into the auto-injector 1 by a small distance. This situation is shown in FIG. 2. During the translation of the needle shroud 3 the bayonet pin 32 on the outer surface of the needle shroud 3 comes into contact with a cam surface 37 in the cam track 33 which causes the outer rear tube 13 to rotate on further depression on the needle shroud 3. This rotation removes the stop 36 obstructing the path of the longitudinal bar 35 of the trigger button 4. The trigger button 4 may now be operated for starting an injection cycle. FIG. 4 illustrates the situation before translation of the needle shroud 3 into the auto-injector 1 in distal direction D. FIG. 5 shows the situation after this translation with the outer rear tube 13 and the stop 36 rotated to allow actuation of the trigger button 4. The compression spring 12 opposes the motion of the needle shroud 3 but is specified such that its spring rate and preload are low enough to feel natural for the user.

Figure 3:
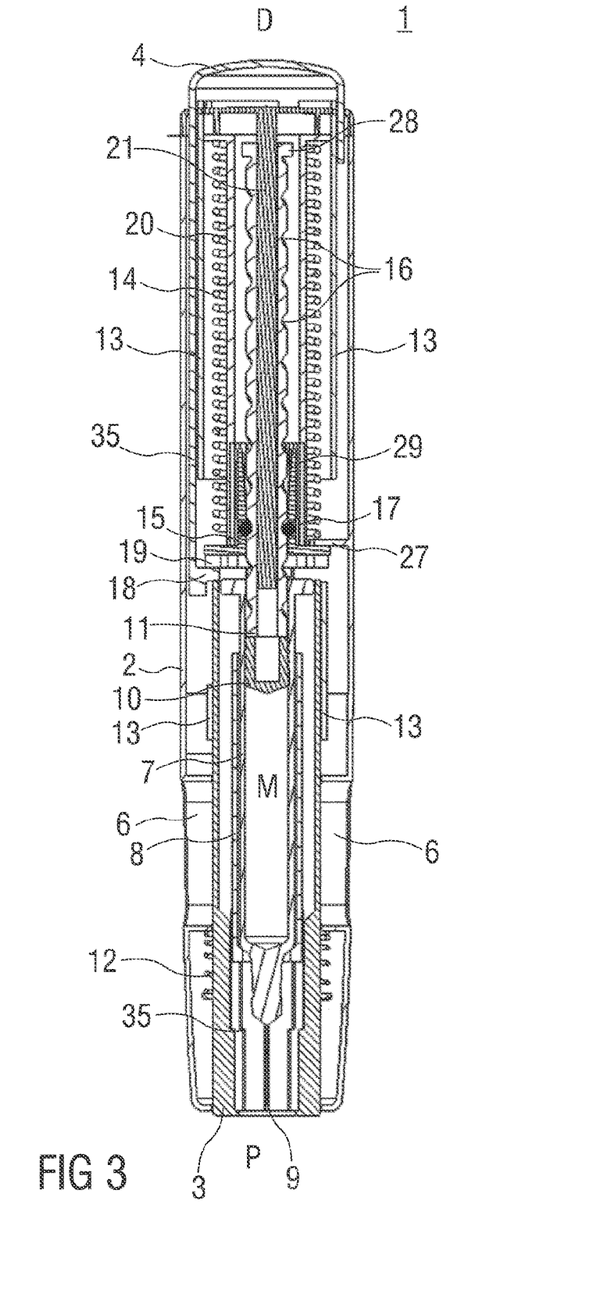
FIG. 3 is a longitudinal section of the auto-injector with the trigger button depressed.
Figure 6:
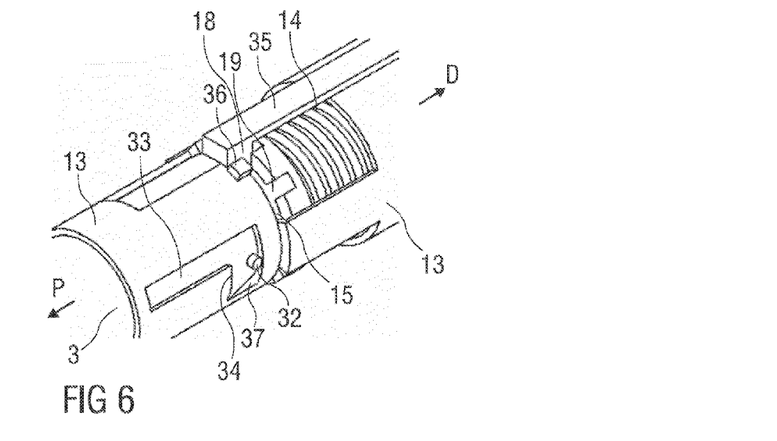
FIG. 6 is a perspective detail view with the trigger button depressed.

FIG. 3 shows the auto-injector 1 with the trigger button 4 depressed. The longitudinal bar 35 is moved in proximal direction P thus moving the locking pin 18 out of the engagement with the dog tooth 19 of the lead nut 15. Thus the lead nut 15 is released and torque from the torsion spring 14 causes the lead nut 15 to rotate. Since the lead nut 15 abuts against a thrust face 27 in the housing 2 it is kept from moving in distal direction D due to the load applied to the piston rod 11 while rotating. FIG. 6 shows the related detail view.

The piston rod 11, kept from rotating by the shaft 21, is pushed forward in proximal direction P due to the engagement of the lead nut 15 and the lead screw thread 16. The advancing piston rod 11 pushes against the bung 10 which in turn advances the syringe 7 by virtue of the friction between the bung 10 and the syringe wall and due to the thin fluid channel inside the hollow needle 9 opposing the displacement of the medicament M. The advancing syringe 7 also causes the needle 9 to protrude beyond the proximal end P of the auto-injector 1 into the injection site, e.g. the patient's skin. Since the syringe 7 is supported at its proximal end by an orifice of the syringe carrier 8 the syringe carrier 8 is also advanced with the syringe 7 until the syringe carrier 8 abuts against an abutment 35 in the needle shroud 3. This contact sets the injection depth relative to the needle shroud 3.

After the syringe carrier 8 has hit the abutment 35 of the needle shroud 3 the syringe 7 is kept from advancing further. With the lead nut 15 still rotating and pushing the piston rod 11 the bung 10 overcomes the friction and the hydraulic resistance of the medicament M and advances inside the syringe 7 thereby displacing the medicament M and delivering it through the fluid channel of the hollow needle 9 into or through the patient's skin.

Figure 7:
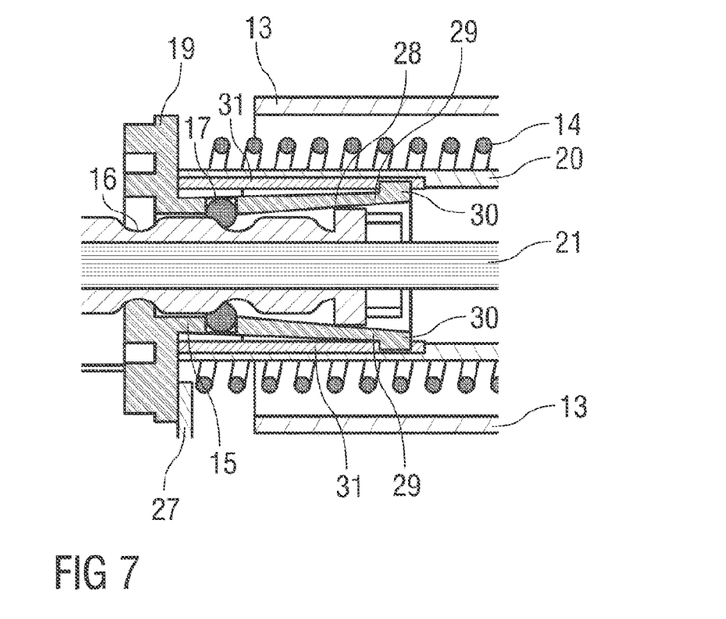
FIG. 7 is a detail longitudinal section illustrating a clutch mechanism.
Figure 8:
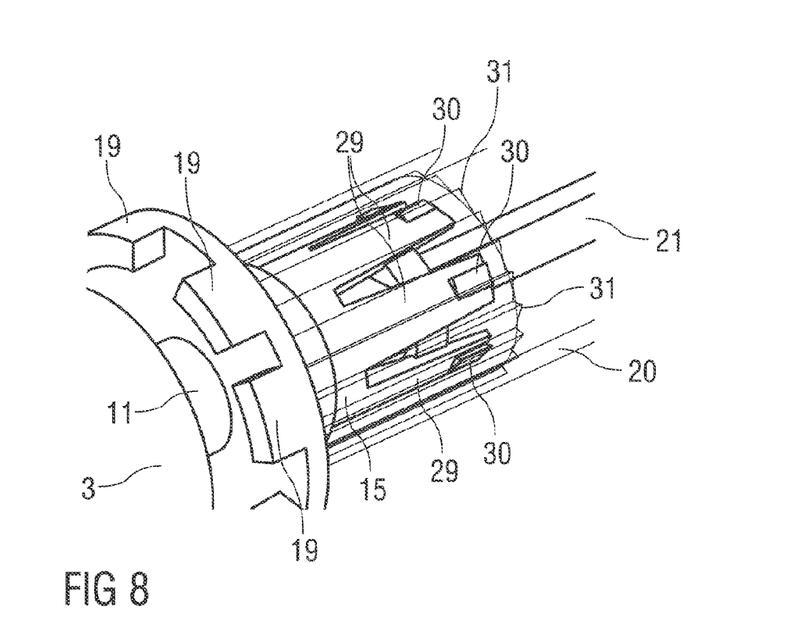
FIG. 8 is a perspective view of one embodiment of the clutch mechanism.

Just before the bung 10 bottoms out in the syringe 7 a shoulder 28 on the distal end of the piston rod 11 behind the lead screw thread 15 is pushed into clutch fingers 29 on the distal end of the lead nut 15 thereby bending the clutch fingers 29 radially outward (see FIG. 7). Each clutch finger 29 has an external tooth 30 which now engages with a respective internal longitudinal spline 31 provided in the proximal end of the inner rear tube 20, causing the inner rear tube 20 to rotate along with the lead nut 15. The splines 31 are arranged in a ratchet manner in FIG. 8.

Figure 9:
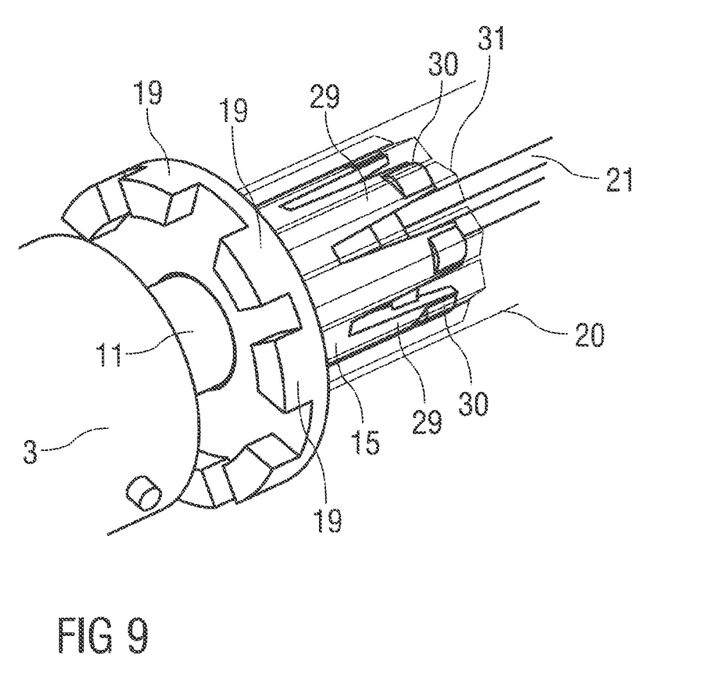
FIG. 9 is a perspective view of another embodiment of the clutch mechanism.

FIG. 9 shows an alternative embodiment with rounded finger teeth 30. In both embodiments (FIGS. 8 and 9) the clutch mechanism is arranged to let the clutch fingers 29 generate enough torque on the longitudinal splines 31 to partially rotate the outer rear tube 13 to release the bayonet fit illustrated in FIGS. 4, 5 and 6. However, the forms of teeth 30 limit the maximum torque that can be transmitted to splines 31, so that the lead nut 15 continues rotating with the clutch fingers 29 jumping over the splines 31 and making a rattling noise indicating that the injection has been nearly finished. The inner rear tube 20 is coupled with the outer rear tube 13 near the distal end D of the auto-injector 1. Thus the outer rear tube 13 is also rotated. The outer tube 13 has a circumferential slot (not illustrated) to allow the distal end of the torsion spring 14 to pass through to the housing 2 for grounding the torsion spring 14. The circumferential slot has to be long enough to allow a partial rotation of the outer rear tube 13 in order to disengage the bayonet fit.

Before the outer rear tube 13 is rotated by the clutch mechanism, the bayonet fit between the pin 32 of the needle shroud 3 and the pin track 33 of the outer rear tube 13 is still in the state as in FIG. 6 with the pin 32 behind a track shoulder 34 so the needle shroud 3 would be held in position against the bias of the compression spring 12 if the still depressed needle shroud 3 was released. A small axial clearance behind the track shoulder 34 allows the needle shroud 3 to be pushed in distal direction D just enough to disengage the interlock between the button 4 and the needle shroud 3 as described above.

When the clutch fingers 29 are engaged with the internal longitudinal splines 31 the outer rear tube 13 is rotated so as to disengage the bayonet fit by the pin 32 coming clear of the track shoulder 34 so the needle shroud 3 may be pushed forward by the compression spring 12. At this point the user is asked to keep pressure with the auto-injector 1 at the injection site for a short period of time, e.g. ten seconds. During this time the lead nut 15 is still rotating and forwarding the piston rod 11 and bung 10 until the bung 10 bottoms out at the proximal end of the syringe 7 thereby virtually entirely displacing the rest of the medicament M from the syringe 7.

As the user withdraws the auto-injector 1 from the injection site the needle shroud 3 is pushed over the needle 9 in proximal direction P by the compression spring 12. A locking mechanism, such as a unidirectional barb or other known to those skilled in the art, may be provided to lock the needle shroud 3 in this forward position in order to prevent re-exposure of the needle.

The auto-injector 1 may preferably be used for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. Auto-injector for administering a dose of a liquid medicament (M), comprising:
   an elongate housing arranged to contain a syringe with a hollow needle and a bung for sealing the syringe and displacing the medicament (M), the elongate housing having a distal end (D) and a proximal end (P) with an orifice intended to be applied against an injection site, wherein the syringe is slidably arranged with respect to the housing,
   a spring capable of, upon activation, pushing the needle from a covered position inside the housing into an advanced position through the orifice and past the proximal end (P) as well as operating the syringe to supply the dose of medicament (M),
   an activator arranged to lock the spring in a pressurized state prior to manual operation and capable of, upon manual operation, releasing the spring for injection,
   wherein the spring is a torsion spring grounded at one end in the housing and at the other end in a first gear member rotatable about a longitudinal axis but axially fixed, wherein the first gear member, upon rotation, is arranged for translatively moving a second gear member, the second gear member being prevented from rotating relative to the housing and coupled to the bung in order to push it towards the proximal end (P), wherein the first gear member is engaged with the activator prior to manual operation in a manner to prevent rotation and disengaged from the activator upon manual operation,
   wherein the activator is a trigger button, arranged at a distal end (D) of the housing and operable by being pressed in proximal direction (P) and the second gear member is a piston rod having an axial bore for slidably arranging the piston rod on a shaft attached to the housing.

2. Auto-injector according to claim 1, characterized in that an essentially tube-shaped needle shroud is arranged around the syringe in the housing, the needle shroud slidable between at least a retracted position with the needle shroud almost hidden inside the housing and an advanced position with the needle shroud protruding from the proximal end (P) and covering the hollow needle in its advanced position, wherein the needle shroud is biased by a second spring towards the advanced position and locked in the retracted position by a lock which is releasable by rotary movement transmitted from the first gear member through a clutch mechanism which is engaged by the second gear member before the second gear member is fully advanced during an injection stroke.

3. Auto-injector according to claim 2, characterized in that an interlock mechanism is arranged for locking the activator and preventing it from being manually operated, wherein the interlock mechanism is coupled to the needle shroud, wherein the interlock mechanism is releasable by pushing the needle shroud a small distance into the housing from the needle shroud's retracted position.

4. Auto-injector according to claim 1, characterized in that the trigger button has a locking pin engageable with at least one dog tooth provided at the first gear member for preventing rotation thereof in order to lock the spring in its pressurized state.

5. Auto-injector according to claim 2, characterized in that the lock has the shape of a bayonet fit between the needle shroud and an outer rear tube arranged around the torsion spring, wherein the needle shroud is guided in the housing in a manner to prevent relative rotation and wherein the outer rear tube is coupled to the clutch mechanism, wherein the bayonet fit comprises a bayonet pin arranged at one of the outer rear tube or the needle shroud and a pin track arranged in the other one of the outer rear tube or the needle shroud.

6. Auto-injector according to claim 1, characterized in that the piston rod has an external lead screw thread, where the axial bore and the shaft having corresponding non-circular profiles, wherein the first gear member is a lead nut engaged with the external lead screw thread.

7. Auto-injector according to claim 6, characterized in that the external lead screw thread has a variable pitch.

8. Auto-injector according to claim 5, characterized in that the interlock mechanism comprises a stop on the outer rear tube arranged to prevent translation of the trigger button prior to the needle shroud being pushed into the housing from the retracted position, wherein the pin track of the bayonet fit comprises a cam surface arranged to be engaged by the bayonet pin on translation of the needle shroud from the retracted position into the housing in such a manner that the outer rear tube is rotated thereby removing the flange so as to allow translation of the trigger button.

9. Auto-injector according to claim 2, characterized in that the syringe is arranged in a syringe carrier and supported by the syringe carrier at a proximal end, wherein the syringe carrier is slidably arranged in the needle shroud and wherein an abutment is provided in the needle shroud defining a maximum forward position of the syringe carrier.

10. Auto-injector according to claim 2, characterized in that the clutch mechanism comprises a circumferential shoulder arranged at the second gear member and at least one resilient clutch finger with a respective inclined inner surface arranged at a distal end of the first gear member, the shoulder arranged for increasingly pressing against the inclined surface thereby flexing the at least one resilient clutch finger outward near the end of an injection stroke, wherein the clutch mechanism further comprises an inner rear tube arranged around the at least one resilient clutch finger inside the torsion spring and attached to the outer rear tube at their distal ends, the inner rear tube having a number of internal longitudinal splines for engaging the flexed-out at least one resilient clutch finger.

11. Auto-injector according to claim 10, characterized in that the internal longitudinal splines are arranged in a manner to form a ratchet when engaged with the at least one resilient clutch finger.

12. Auto-injector according to claim 2, characterized in that a locking mechanism is provided for locking the needle shroud in its advanced position.

13. Auto-injector according to claim 1, characterized in that at least one viewing window for inspecting the syringe is provided in the housing (2).

14. Auto-injector according to claim 6, characterized in that the lead nut is provided with at least one pin or with a ball bearing for engaging the external lead screw thread.

* * * * *